United States Patent
Tanaka et al.

(10) Patent No.: US 7,601,971 B2
(45) Date of Patent: Oct. 13, 2009

(54) CHARGED BEAM GUN

(75) Inventors: Takeshi Tanaka, Hitachi (JP); Hiroyasu Kaga, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 134 days.

(21) Appl. No.: 11/954,401

(22) Filed: Dec. 12, 2007

(65) Prior Publication Data

US 2008/0135756 A1 Jun. 12, 2008

(30) Foreign Application Priority Data

Dec. 12, 2006 (JP) ............... 2006-334370

(51) Int. Cl.
- H01J 37/073 (2006.01)
- H01J 49/08 (2006.01)
- H01J 49/10 (2006.01)

(52) U.S. Cl. ............... 250/423 F; 250/423 R; 250/430; 250/493.1; 315/111.81

(58) Field of Classification Search ............ 250/423 F, 250/423 R, 430, 493.1; 315/111.81
See application file for complete search history.

(56) References Cited

U.S. PATENT DOCUMENTS

| | | | | |
|---|---|---|---|---|
| 4,563,587 A | * | 1/1986 | Ward et al. ............... | 250/396 R |
| 6,107,628 A | * | 8/2000 | Smith et al. ............... | 250/292 |
| 7,138,629 B2 | * | 11/2006 | Noji et al. ............... | 250/311 |
| 2009/0101816 A1 | * | 4/2009 | Noji et al. ............... | 250/310 |

FOREIGN PATENT DOCUMENTS

| JP | 2002-270125 A | 9/2002 |
|---|---|---|
| JP | 2004-349155 A | 12/2004 |

OTHER PUBLICATIONS

Japanese Office Action dated Dec. 9, 2008 (Six (6) pages).

* cited by examiner

*Primary Examiner*—Nikita Wells
(74) *Attorney, Agent, or Firm*—Crowell & Moring LLP

(57) ABSTRACT

The present invention provides a highly reliable charged beam gun designed in consideration for environmental protection, which prevents faulty insulation in a high-voltage connection. An insulating liquid is present in a gap formed between a connecting bushing and a receiving-side flange placed in a vacuum container, and the connecting bushing includes first piping and valve that provide communication between the gap and atmospheric air, and second piping and valve that provide communication between the gap and the atmospheric air, whereby the gap is cut off from the atmospheric air.

9 Claims, 4 Drawing Sheets

CHARGED BEAM GUN

CLAIM OF PRIORITY

The present application claims priority from Japanese application JP 2006-334370 filed on Dec. 12, 2006, the content of which is hereby incorporated by reference into this application.

BACKGROUND OF THE INVENTION

1. Field of the Invention

The present invention relates to a charged beam gun where a high positive voltage is applied in order to accelerate charged particles, such as a field emission type electron gun of a scanning electron microscope system.

2. Description of the Related Art

For a charged beam gun for an apparatus of which a high ultimate vacuum and a good-quality vacuum are required, such as an electron beam apparatus and an ion beam apparatus, vacuum degassing (or baking) of the charged beam gun is performed in order to achieve a high-level and good-quality vacuum in the body thereof. Here, having regard to thermal resistance of the charged beam gun, maintenance of the charged beam gun, and so on, a high-voltage cable unit and a vacuum container that is the body of the charged beam gun are configured as separate structures. Accordingly the charged beam gun has a structure configured by assembling the above-mentioned two portions and connecting a high-voltage power supply unit to the assembly. Dielectric strength of a section that provides an electrical connection between a power supply part and a body part is important for such a charged beam gun.

The related art for increasing the dielectric strength is, for example, to employ a method in which space for the electrical connection between the power supply part and the body part is provided to increase a creepage distance. Moreover, as another prior art, it is suggested to fill an insulating liquid having fluorine as a main ingredient into the space for the electrical connection between the power supply part and the body part, as disclosed in Japanese Patent Application Laid-open Publication

SUMMARY OF THE INVENTION

The above related art method in which a gap is provided in the vicinity of the high-voltage connection to increase the creepage distance requires a size of the gap and a creepage distance that are sufficient to keep predetermined dielectric strength, resulting in an obstacle to downsizing the body of the charged beam gun. Further, changes in the charged beam gun's surrounding environment can possibly cause condensation on or moisture absorption into a high-voltage insulating surface and thus lead to an increase in leakage current into an insulating area and hence to a decrease in the dielectric strength. However, the filling of the insulating liquid having the fluorine as the main ingredient into the space for the electrical connection between the power supply part and the body part permits curbing the increase in the leakage current resulting from the condensation on or the moisture absorption into the high-voltage insulating surface, and thereby enables an improvement of the dielectric strength and thus achieving a miniaturizable, highly-reliable charged beam gun. However, this charged beam gun does not have an environmentally-friendly design, because of being designed without consideration for the filling or recovery of the insulating liquid, which are important for an apparatus that handles chemical materials. No particular consideration is given to the prevention of depletion of ozone layer, global warming, or air pollution.

An object of the present invention is to provide a charged beam gun with a high reliability of insulation and with a lighter load on the environment, by preventing faulty insulation in a high-voltage connection of the charged beam gun including an ultra-high vacuum container requiring the insertion and removal of a connecting bushing.

To achieve the above object, the present invention provides a configuration in which an insulating liquid (e.g., perfluorocarbon) having fluorine as a main ingredient is filled into a connection space for the electrical connection between the power supply part and the body part, and the connection space is completely shielded from the outside air by piping and a valve of a connecting bushing.

The above configuration can suppress an increase in leakage current resulting from condensation on or moisture absorption into the surface of an insulating material in the vicinity of a high-voltage connection of a charged beam gun in an ultra-high vacuum container, thereby improve dielectric strength, and thus achieve a size-reducible, highly reliable charged beam gun. Moreover, this configuration enables the charging of the insulating liquid into the connection space and the discharge, recovery and reuse of the insulating liquid from the connection space without having to disconnect the connecting bushing.

The present invention can prevent a decrease in insulation resistance of a creepage surface of an insulator resulting from condensation or moisture absorption due to changes in use environment of the apparatus, thus suppress an increase in leakage current, thus maintain dielectric strength over the long term, and thus improve stable operability of the apparatus. Moreover, the present invention can achieve a small-size charged beam gun highly reliable in dielectric strength and appropriate for environmental protection.

DETAILED DESCRIPTION OF THE INVENTION

An embodiment of the present invention will be described below with reference to the drawings.

Figure 1:
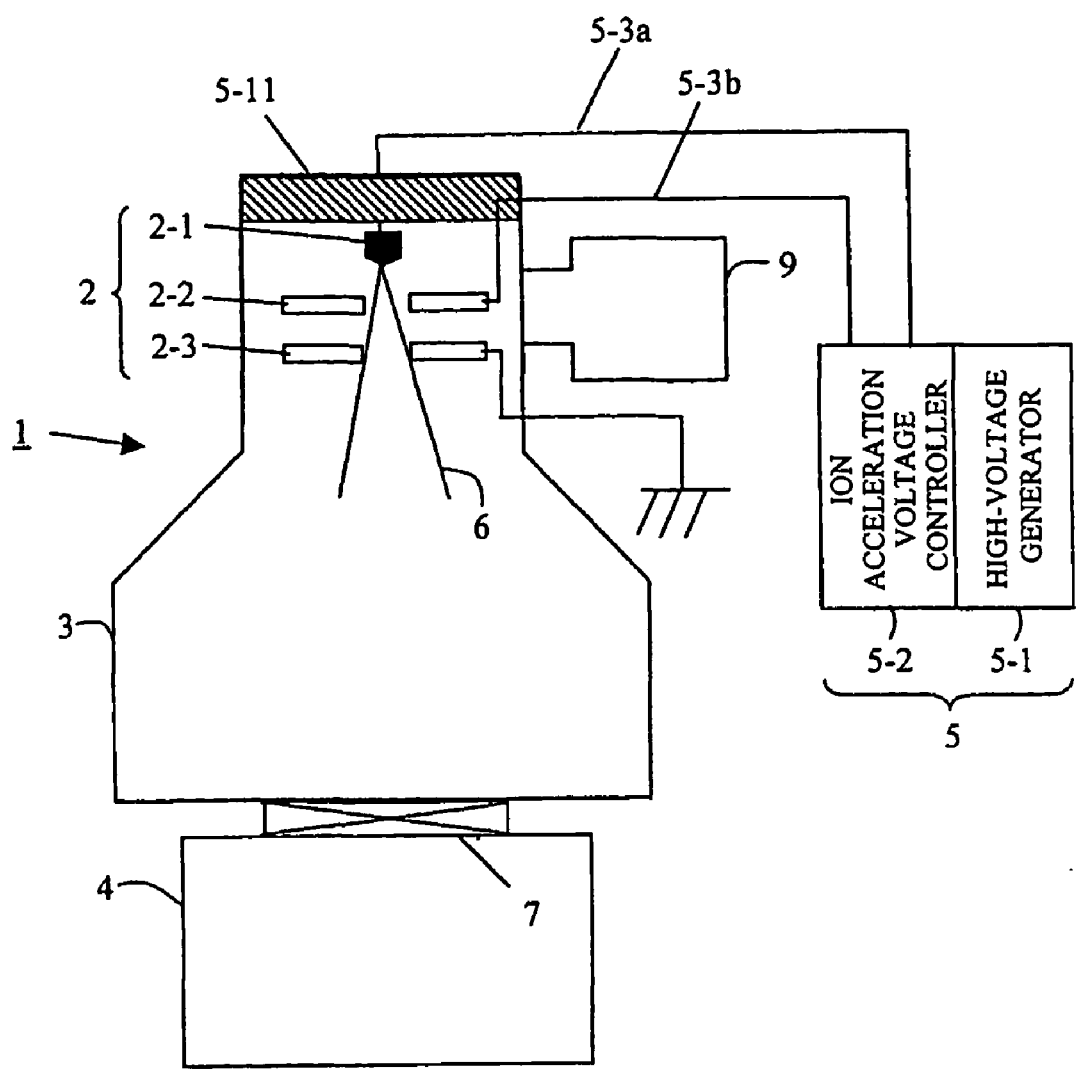
FIG. 1 is a schematic view of the configuration of an ion beam apparatus according to one embodiment of a charged beam gun of the present invention.

FIG. 1 is a schematic view of the configuration of an ion beam apparatus according to one embodiment of a charged beam gun of the present invention. An ion beam apparatus 1 according to the embodiment includes an ion gun 2, a vacuum container 3, a vacuum pumping system 4, and a high-voltage power supply unit 5. A gate valve 7 is interposed between the vacuum container 3 and the vacuum pumping system 4. The ion gun 2 includes an ion source 2-1, an extraction electrode 2-2, and an acceleration electrode 2-3. The ion gun 2 contained within the vacuum container 3 is evacuated by an ion pump 9. Moreover, the high-voltage power supply unit 5 includes a high-voltage generator 5-1 for ion acceleration and an ion acceleration controller 5-2, and the high-voltage power supply unit 5 applies a high positive voltage to the ion source 2-1 via a high-voltage cable 5-3a and applies a high positive voltage to the extraction electrode 2-2 via a high-voltage cable 5-3b. The acceleration electrode 2-3 is grounded. An ion beam 6 extracted from the ion source 2-1 by the extraction electrode 2-2 is accelerated by the acceleration electrode 2-3 and is irradiated downstream. A focused ion beam system for processing or observation can be configured by adding, to the ion beam apparatus 1, a signal detection system for detecting a signal obtained by irradiating an ion beam on a specimen and a function of irradiating an ion beam on a specimen after narrowing an ion beam to be irradiated with lens while controlling deflection of the ion beam.

Figure 2:
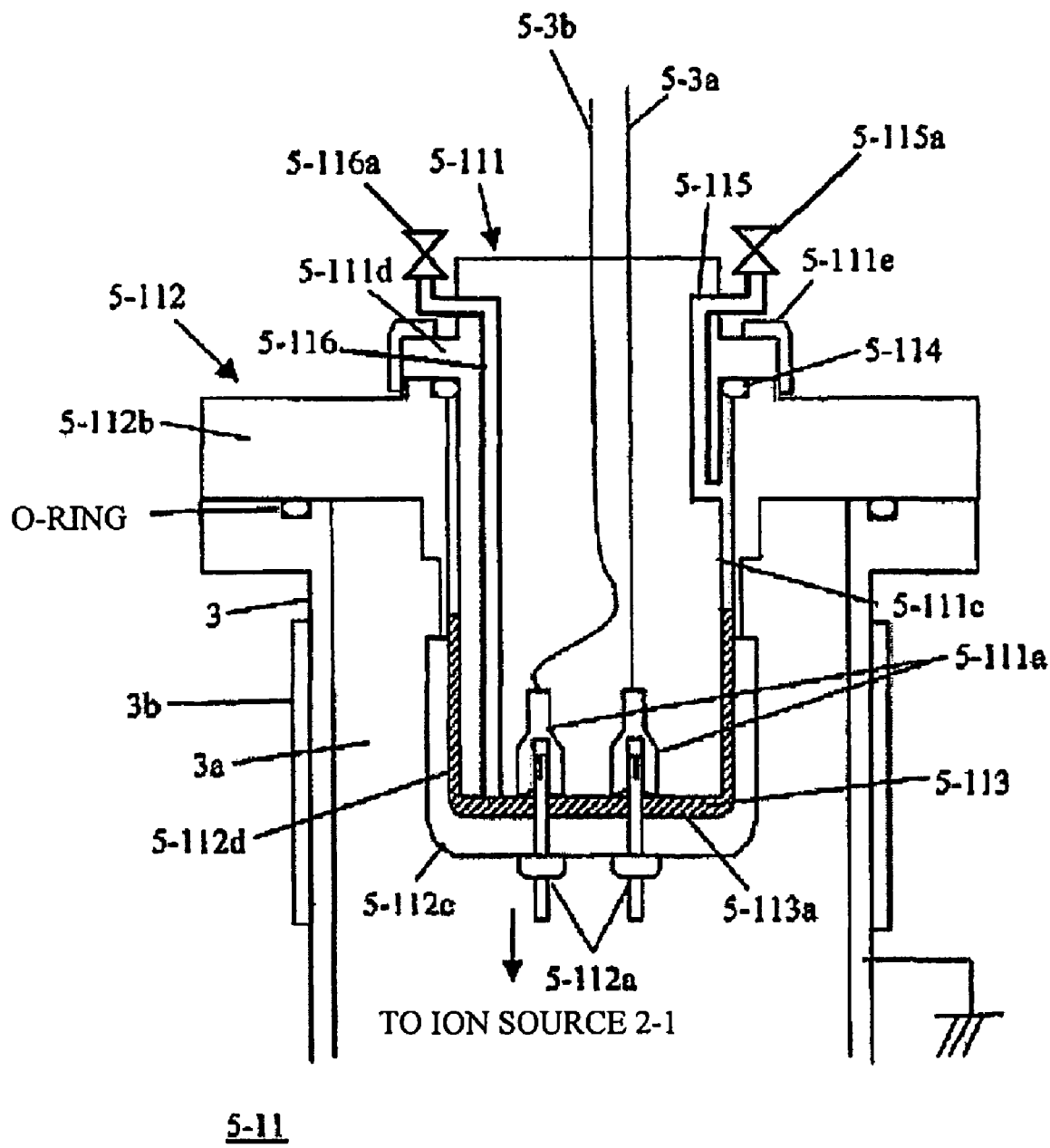
FIG. 2 is a cross-sectional view of a high-voltage connection of an ion gun according to the present invention.
Figure 3:
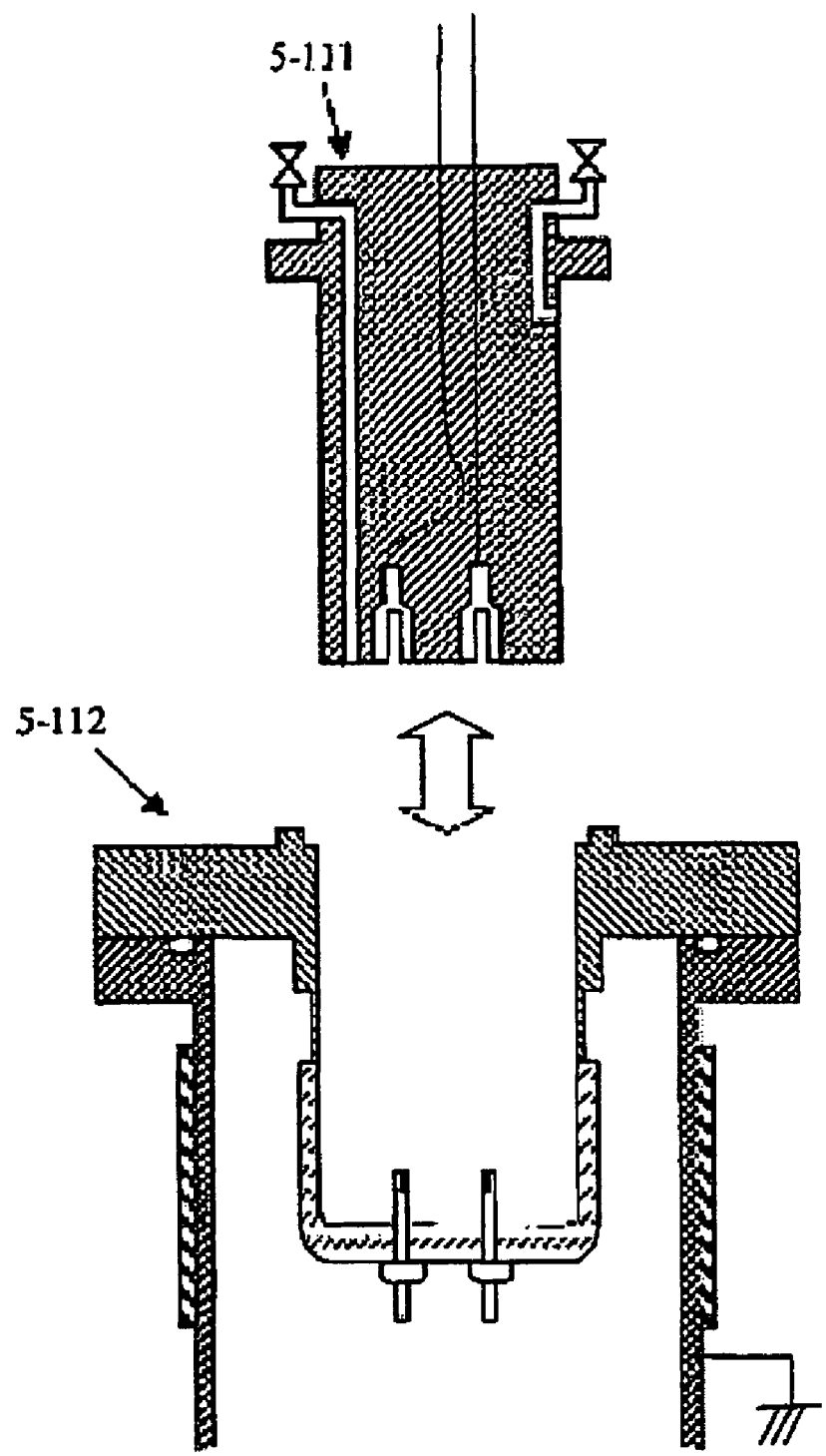
FIG. 3 is a view of the high-voltage connection with its connecting bushing disconnected from its receiving-side flange.

FIG. 2 is a cross-sectional view of a high-voltage connection of the ion gun according to the present invention, and FIG. 3 is a view of the high-voltage connection with its connecting bushing disconnected from its receiving-side flange.

The vacuum container 3 is provided with a heater 3b for vacuum degassing. While being heated by the heater 3b, the vacuum container 3 is evacuated to attain a vacuum on the order of $10^{-6}$ Pa. Incidentally, the vacuum container 3 is not limited to being provided with the heater, and other means may be used to evacuate the vacuum container 3 while heating it. The high voltage generated by the high-voltage generator 5-1 is applied to bushing terminals 5-111a of a feeding-side connecting bushing 5-111 via the high-voltage cables 5-3a and 5-3b. And after further applied to flange terminals 5-112a of a receiving-side flange 5-112 closely connected with the feeding-side connecting bushing 5-111, the high voltage generated by the high-voltage generator 5-1 is lead to the ion source 2-1 shown in FIG. 1. The top portion of the receiving-side flange 5-112 is formed of a metallic flange 5-112b, which is at a ground potential. Moreover, the bottom portion of the receiving-side flange 5-112 is formed of an insulator 5-112c, which provides insulation between the ground potential of the metallic flange 5-112b and the high voltage applied to the flange terminals 5-112a or the feeding-side bushing terminals 5-111a. The high voltage is impressed across either the bushing terminals 5-111a or the receiving-side flange terminals 5-112a and the metallic flange 5-112b.

A gap 5-113 at around 1 mm is provided between the feeding-side connecting bushing 5-111 and the receiving-side flange 5-112, and the gap 5-113 is partially filled with an insulating liquid 5-113a having a low content of moisture dissolved therein (hereinafter referred to simply as an "insulating liquid"). The connecting bushing 5-111 is provided with piping 5-115 and a valve 5-115a for regulating an internal pressure in the gap 5-113. A one-way opening type valve can be used for the valve 5-115a. The connecting bushing 5-111 is further provided with piping 5-116 and a valve 5-116a for the filling and recovery of the insulating liquid 5-113a. When a bushing flange 5-111d of the connecting bushing 5-111 is fixed with a bushing presser 5-111e, the insulating liquid 5-113a is cut off from the outside air by an O-ring 5-114 and the valve 5-115a.

The high-voltage cables 5-3a and 5-3b via which the high voltage is fed to a power-receiving unit are held in the connecting bushing 5-111 made of an insulating resin. The connecting bushing 5-111 is removably fitted in the receiving-side flange 5-112 provided for the vacuum container 3. The bushing terminals 5-111a, which are provided for the connecting bushing 5-111 and connected to the cables 5-3a and 5-3b, are disengageably connected to the flange terminals 5-112a, which are provided for the receiving-side flange 5-112 and lead power to the power receiving unit. The disengageable connection is performed on the removal of the connecting bushing 5-111 from the power receiving unit. (See FIG. 3.)

Figure 4:
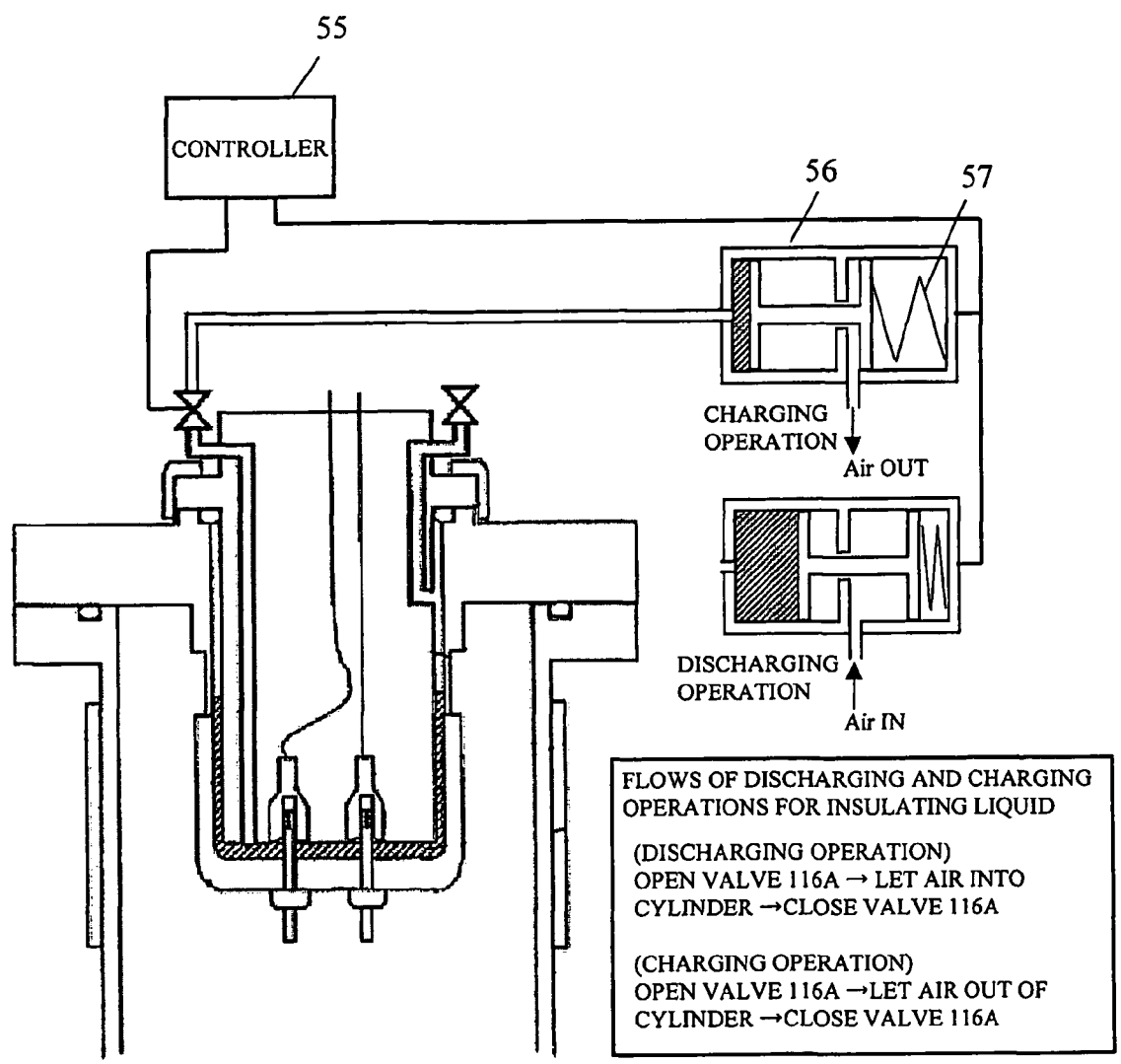
FIG. 4 is a view showing a method for charging and discharging an insulating liquid, using a pneumatic piston mechanism.

When the connecting bushing 5-111 is fitted in the receiving-side flange 5-112, the insulating liquid 5-113a having the low content of moisture dissolved therein is filled into the gap 5-113 formed between the connecting bushing 5-111 and the receiving-side flange 5-112. The filling of the insulating liquid 5-113a is accomplished by opening the valve 5-116a with the connecting bushing 5-111 fitted in the receiving-side flange 5-112, and charging the insulating liquid 5-113a into the gap 5-113 through the piping 5-116 formed through the connecting bushing 5-111. Incidentally, a rise in the internal pressure in the gap 5-113 during the filling leads to the opening of the valve 5-115a, resulting in the release of the internal pressure in the gap 5-113. As opposed to the filling, the recovery of the insulating liquid 5-113a is accomplished by opening the valve 5-115a and the valve 5-116a, and sucking up the insulating liquid 5-113a through the piping 5-116 formed through the connecting bushing 5-111, and after the recovery, the valve 5-115a and the valve 5-116a are closed. After that, the connecting bushing 5-111 is disconnected from the receiving-side flange 5-112 to thereby avoid exposure of the insulating liquid 5-113a. A pneumatic piston mechanism 56 having a spring 57 built-in as shown for example in FIG. 4 is used for the charging or suction of the insulating liquid 5-113a. Moreover, the valve 5-115a may be formed of a one-way opening type valve designed to be closed under normal pressure and be opened under an increased internal pressure.

A cylinder of the piston mechanism 56 is separated into a cylinder chamber having the spring 57 built-in and a chamber containing the insulating liquid as shown in FIG. 4. Operation of a cylinder unit shown in FIG. 4 for charging the insulating liquid 5-113a involves opening the valve 5-115a and the valve 5-116a in the piping, letting air out of the chamber having the spring built-in, pressing a piston of the cylinder by the spring, forcing the insulating liquid out of the cylinder, filling the insulating liquid into the gap 5-113 through the piping 5-116, and closing the valve 5-115a and the valve 5-116a. As opposed to this, the discharge and recovery of the insulating liquid 5-113a from the gap 5-113 involves opening the valve 5-116a in the piping 5-116, letting air into the cylinder, pulling the piston, recovering the insulating liquid into the cylinder through the piping 5-116, and thereafter closing the valve 5-116a. Pneumatic operation of the piston mechanism 56 and control of the valves 5-115a and 5-116a are performed by a controller 55. When a one-way opening type valve is used for the valve 5-116a, it is not necessary to control the valve 5-116a.

With this, when the apparatus is under operation, the insulating liquid 5-113a is present in the gap 5-113 in the vicinity of the high-voltage connection in which the bushing terminals 5-111a are connected to the flange terminals 5-112a. The presence of the insulating liquid enables suppressing an increase in leakage current resulting from condensation or moisture absorption and a decrease in dielectric strength resulting from the increase in the leakage current. In other words, the presence of the insulating liquid enables improvement of the dielectric strength and hence the reliability, by suppressing the increase in the leakage current even if changes in ambient atmosphere occur and thus cause condensation on or moisture absorption into a insulating surface 5-111c of the bushing or a insulating surface 5-112d of the receiving-side flange. Moreover, the bushing is provided with the piping, and thereby the insulating liquid 5-113a can be charged into or discharged and recovered from the gap 5-113, as being cut off from the outside (or without leaking out). Furthermore, for example when the piping is formed merely by drilling directly through the bushing, the bushing can be configured so that there is little change in dielectric properties therein even if it has the piping, and therefore the presence of the piping presents no structural defect.

Stable beam emission from a charged beam source requires high-level and good-quality vacuum. Thus, the vacuum container 3 is provided with the heater 3b for degassing of the container. Heating of the heater 3b for degassing is called "baking," and mention will be made of the handling of the insulating liquid during the baking. The baking is performed after the removal of the insulating liquid 5-113a.

In the embodiment, FC-75 (Fluorinert manufactured by Sumitomo 3M Ltd.) is used as the insulating liquid 5-113a. The FC-75 is an inert solution made of perfluorocarbon (PFC) having a molecular structure of $C_8F_{16}$, its dielectric strength is five or more times the dielectric strength of air (3 kV/mm) (that is, the dielectric strength is equal to or more than 15 kV/mm), and it exhibits insulating properties comparable to those of mineral oil used in an isolation transformer or the like. Other features of the PFC include good thermal conductivity, low surface tension, and inertness. The PFC is an environmentally-friendly substance because, although having about the same volatility as alcohol, the PFC has no toxicity, little ozone-depleting effect and little global-warming effect. However, the fact that depletion of ozone layer, global warming, or air pollution causes great changes in the global environment has recently become a problem. Thus, it is required that the apparatus be designed taking into account the minimization of load on the environment. This respect is important particularly for an apparatus that handles chemical materials. Thus, the apparatus of the present invention enables the charging, discharge, recovery and reuse of the PFC as cut off from the outside world.

The PFC is also easy to reuse because of being inert and thus undergoing no change in physical properties with time. Even if the PFC erroneously adheres to an ultra-high vacuum component that is easily affected by contamination, the PFC is evaporated spontaneously and volatilized without any impurity remaining, and thus, there is no fear of the vacuum component being contaminated by the PFC, so that the PFC can be used for the charged beam gun such as an ion gun or an electron gun. Moreover, the PFC does not affect the physical properties of structural components of the ion gun. The use of the PFC as charged into a gap space at the joint between the high-voltage cables and the bushing of the present invention makes it possible to prevent a decrease in surface resistance of an insulating material, which occurs under the influence of ambient temperature or humidity when the surface of the insulating material is contaminated or damaged.

Incidentally, discussion will be made with regard to the fact that the dielectric strength of the surface of the insulating material such as the insulator decreases under the influence of humidity. Since water in itself has a high dielectric constant (70 to 90) and moreover a great variety of substances can dissolve in the water, the material that has absorbed moisture suffers from a decrease in insulation resistance caused by the water. The surface resistance of the insulating material decreases, in particular when water having an ionic substance dissolved therein adheres to the surface of the insulating material or when water adheres to the contaminated surface of the insulating material and contaminants are dissolved in the water. Actually, the insulation resistance of a contaminated or damaged portion of the bushing decreases under the influence of humidity, and as a result, the bushing partially becomes a resistor. A current passes through a high-resistance resistor in a portion having an intense electric field and relaxes the electric field, and thus a minute surface current is developed, resulting in a trace of electric discharge being left in the connecting bushing. The use of the PFC makes it possible to prevent such faulty insulation.

With the ion gun used in an experiment, the entire high-voltage unit was submerged as shown in FIG. 2 by charging 15 cc of PFC. When water is dissolved in the PFC (incidentally, saturated water absorption is 11 ppm (wt) at 25° C.), the dielectric strength decreases, but this decrease has little influence and thus a dielectric breakdown voltage exceeds 15 kV/mm. Therefore, the dielectric breakdown voltage of the PFC exceeds 15 kV/mm even if water dissolves in the PFC to reach the saturated water absorption, provided that the ion gun is used around room temperature. In this respect, the PFC is significantly different from insulating oil in an amount of change in the dielectric breakdown voltage relative to water dissolution. Under a condition where water floats, however, droplets of the water move around by electrostatic induction, resulting in a decrease in the dielectric strength.

What is claimed is:

1. A charged beam apparatus, comprising:
   a vacuum container housing a charged beam gun;
   a heater that heats the vacuum container;
   a connecting bushing having at its bottom a bushing terminal connected to a cable via which a high voltage is fed to the charged beam gun; and
   a receiving-side flange provided for the vacuum container and having a flange terminal to be connected to the bushing terminal, which removably supports the connecting bushing,
   wherein an insulating liquid is charged into a gap formed between the receiving-side flange and the connecting bushing,
   the connecting bushing is provided with first piping and second piping that provide communication between the gap and atmospheric air, and the first piping and the second piping are each provided with a valve.

2. The charged beam apparatus according to claim 1, wherein the first piping has an opening in the bottom of the connecting bushing.

3. The charged beam apparatus according to claim 2, comprising:
   a piston mechanism connected to the first piping; and
   a controller that controls the piston mechanism and the valve provided for the first piping,
   wherein the controller controls the piston mechanism and the valve for suction and discharge of the insulating liquid from the gap.

4. The charged beam apparatus according to claim 3, wherein the valve provided for the second piping is a one-way opening type valve.

5. The charged beam apparatus according to claim 2, wherein the first piping and the second piping are made of a material having the same dielectric constant as the connecting bushing.

6. The charged beam apparatus according to claim 2, wherein the openings, toward the gap, of the first piping and the second piping are disposed at different levels above the bottom of the connecting bushing.

7. The charged beam apparatus according to claim 1, wherein the first piping and the second piping are made of a material having the same dielectric constant as the connecting bushing.

8. The charged beam apparatus according to claim 7, wherein the openings, toward the gap, of the first piping and the second piping are disposed at different levels above the bottom of the connecting bushing.

9. The charged beam apparatus according to claim 1, wherein the openings, toward the gap, of the first piping and the second piping are disposed at different levels above the bottom of the connecting bushing.

* * * * *